(12) United States Patent
Balslev et al.

(10) Patent No.: US 11,449,718 B2
(45) Date of Patent: Sep. 20, 2022

(54) METHODS AND SYSTEMS OF REAL TIME MOVEMENT CLASSIFICATION USING A MOTION CAPTURE SUIT

(71) Applicants: Jakob Balslev, Copenhagen (DK); Anders Kullmann Klok, Copenhagen (DK); Maziar Taghiyar-Zamani, Copenhagen (DK); Matias Søndergaard, Copenhagen (DK); Lasse Petersen, Copenhagen (DK); Peter Jensen, Copenhagen (DK)

(72) Inventors: Jakob Balslev, Copenhagen (DK); Anders Kullmann Klok, Copenhagen (DK); Maziar Taghiyar-Zamani, Copenhagen (DK); Matias Søndergaard, Copenhagen (DK); Lasse Petersen, Copenhagen (DK); Peter Jensen, Copenhagen (DK)

(*) Notice: Subject to any disclaimer, the term of this patent is extended or adjusted under 35 U.S.C. 154(b) by 0 days.

(21) Appl. No.: 17/068,809

(22) Filed: Oct. 12, 2020

(65) Prior Publication Data
US 2021/0374486 A1 Dec. 2, 2021

Related U.S. Application Data

(63) Continuation of application No. 16/111,168, filed on Aug. 23, 2018, now Pat. No. 10,949,716, which is a
(Continued)

(51) Int. Cl.
*G06K 9/62* (2022.01)
*G06N 20/10* (2019.01)
(Continued)

(52) U.S. Cl.
CPC ............ *G06K 9/6269* (2013.01); *G06F 3/011* (2013.01); *G06F 17/142* (2013.01); *G06N 20/10* (2019.01); *G06V 40/23* (2022.01)

(58) Field of Classification Search
CPC .. G06K 9/6269; G06K 9/00342; G06N 20/10; G06F 3/011; G06F 3/017;
(Continued)

(56) References Cited

U.S. PATENT DOCUMENTS 8,929,600 B2* 1/2015 Liu .................... G06K 9/00342
382/103
10,324,522 B2* 6/2019 Balslev ................. A63F 13/428
(Continued)

*Primary Examiner* — Tom V Sheng

(57) ABSTRACT

In one aspect, a computerized process useful for movement classification using a motion capture suit includes the step of providing the motion capture suit worn by a user. The motion capture suit comprises a set of position sensors and a Wi-Fi system configured to communicate a set of position sensor data to a computing system. The process includes the step of providing the computing system to: receive a set of position data from the motion capture suit for a specified time window of data comprising X, Y and Z axis positions and a joints-angle data for each position sensor of the set of position sensors, transforming each joints-angle data to a corresponding frequency domain using a fast Fourier transformation to remove any time dependency value, after the fast Fourier data transformation, train a support vector machine using the X, Y and Z axis positions data and the frequency domain data as input, using the support vector machine to predict a set of body positions and movements.

20 Claims, 9 Drawing Sheets

Related U.S. Application Data continuation-in-part of application No. 15/361,347, filed on Nov. 25, 2016, now Pat. No. 10,324,522.

(60) Provisional application No. 62/549,309, filed on Aug. 23, 2017, provisional application No. 62/260,248, filed on Nov. 25, 2015.

(51) Int. Cl.
*G06F 17/14* (2006.01)
*G06F 3/01* (2006.01)
*G06V 40/20* (2022.01)

(58) Field of Classification Search
CPC .... G06F 17/142; A63F 13/211; A63F 13/212; A63F 13/213; A63F 13/25; A63F 13/428; A63F 13/5255; A63F 2300/1043; A63F 2300/105; A63F 2300/8082; G06T 7/20; G06T 13/40; H05K 999/99
USPC .......................................................... 345/156
See application file for complete search history.

(56) References Cited

U.S. PATENT DOCUMENTS

| | | | |
|---|---|---|---|
| 10,949,716 B2* | 3/2021 | Balslev | G06N 20/10 |
| 2006/0274070 A1* | 12/2006 | Herman | A63F 13/10 |
| | | | 345/474 |
| 2008/0285805 A1* | 11/2008 | Luinge | A61B 5/1122 |
| | | | 382/107 |
| 2009/0322763 A1* | 12/2009 | Bang | G06K 9/00342 |
| | | | 345/474 |
| 2010/0290538 A1* | 11/2010 | Xu | G06T 13/205 |
| | | | 375/240.28 |
| 2013/0222565 A1* | 8/2013 | Guerin | G06F 3/0346 |
| | | | 348/77 |
| 2015/0309563 A1* | 10/2015 | Connor | A61B 5/1071 |
| | | | 73/865.4 |
| 2015/0366504 A1* | 12/2015 | Connor | A61B 5/6804 |
| | | | 600/301 |
| 2016/0202755 A1* | 7/2016 | Connor | A41D 13/1281 |
| | | | 73/865.4 |
| 2016/0338644 A1* | 11/2016 | Connor | A61B 5/11 |
| 2018/0216959 A1* | 8/2018 | Dai | B81B 7/02 |

* cited by examiner

RECORD A TIME WINDOW OF DATA CONSISTING OF THE SENSORS X, Y AND Z POSITIONS AND THE JOINTS ANGLES
102

TRANSFORM THE ANGLES TO THEIR CORRESPONDING FREQUENCY DOMAIN USING FAST FOURIER TRANSFORMATION TO GET RID OF THE TIME DEPENDENCY
104

TRAIN A SUPPORT VECTOR MACHINE USING THE X,Y,Z DATA AND THE FREQUENCY DATA AS INPUT
106

USE THE SUPPORT VECTOR MACHINE TO PREDICT THE BODY POSITIONS AND MOVEMENTS IN REAL TIME WITH COMPELLING RESULTS
108

| Frame | $0 - p_x$ | ... | $18 - \Theta$ | Hub Time |
|---|---|---|---|---|
| 1 | -0.001026886 | ... | 12.38563 | 459.173 |
| 2 | -0.001026886 | ... | 12.38563 | 459.173 |
| 3 | -0.001026886 | ... | 12.38563 | 459.173 |

METHODS AND SYSTEMS OF REAL TIME MOVEMENT CLASSIFICATION USING A MOTION CAPTURE SUIT

CLAIM OF PRIORITY AND INCORPORATION BY REFERENCE

This application claims priority from U.S. application Ser. No. 17068809, title METHODS AND SYSTEMS OF A MOTION-CAPTURE BODY SUIT WITH WEARABLE BODY-POSITION SENSORS and filed Oct. 12, 2020. This application is hereby incorporated by reference in its entirety for all purposes.

U.S. Application Ser. No. 17068809 claims priority from U.S. Application Ser. No. 16111168, title METHODS AND SYSTEMS OF A MOTION—CAPTURE BODY SUIT WITH WEARABLE BODY-POSITION SENSORS and filed Aug. 23, 2018. This application is hereby incorporated by reference in its entirety for all purposes.

U.S. application Ser. No. 16111168 claims priority from U.S. application Ser. No. 15/361,347, title METHODS AND SYSTEMS OF A MOTION-CAPTURE BODY SUIT WITH WEARABLE BODY-POSITION SENSORS and filed Nov. 25, 2016. This application is hereby incorporated by reference in its entirety for all purposes.

This application claims priority from U.S. application Ser. No. 15/361,347, title METHODS AND SYSTEMS OF REAL TIME MOVEMENT CLASSIFICATION USING A MOTION CAPTURE SUIT and filed Aug. 23, 2017. This application is hereby incorporated by reference in its entirety for all purposes.

FIELD OF THE INVENTION

The invention is in the field of motion sensing and analysis and more specifically to a method, system and apparatus of real time movement classification using a motion capture suit.

DESCRIPTION OF THE RELATED ART

Problems can arise when classifying different body positions and movements using only data from sensors positioned on the body (e.g. no visual data). Accordingly, improvements to classifiers to distinguish between static positions and dynamic movements are desired.

SUMMARY

In one aspect, a computerized method useful for hand movement classification using a motion capture glove includes the step of providing a motion capture glove comprises one or multiple sensors connected to a back of the motion capture glove and one or multiple sensors connected to each finger of the motion capture glove. The method includes the step of, with the one or multiple sensors, measuring a set of physical quantities that describe a motion and a pose of a hand wearing the motion capture glove.

In another aspect, a computerized process useful for movement classification using a motion capture glove includes the step of providing the motion capture glove worn by a user. The motion capture glove comprises a set of position sensors and a Wi-H system configured to communicate a set of position sensor data to a computing system. The process includes the step of providing the computing system to: receive a set of position data from the motion capture glove for a specified time window of data comprising X, Y and Z axis positions and a joints-angle data for each position sensor of the set of position sensors, transforming each joints-angle data to a corresponding frequency domain using a fast Fourier transformation to remove any time dependency value, after the fast Fourier data transformation, train a support vector machine using the X, Y and Z axis positions data and the frequency domain data as input, using the support vector machine to predict a set of body positions and movements.

BRIEF DESCRIPTION OF THE DRAWINGS

FIG. 1 illustrates an example process for real time movement classification using a motion capture suit, according to some embodiments.

FIG. 3 illustrates an example table, according to some embodiments,

Figure 2A:
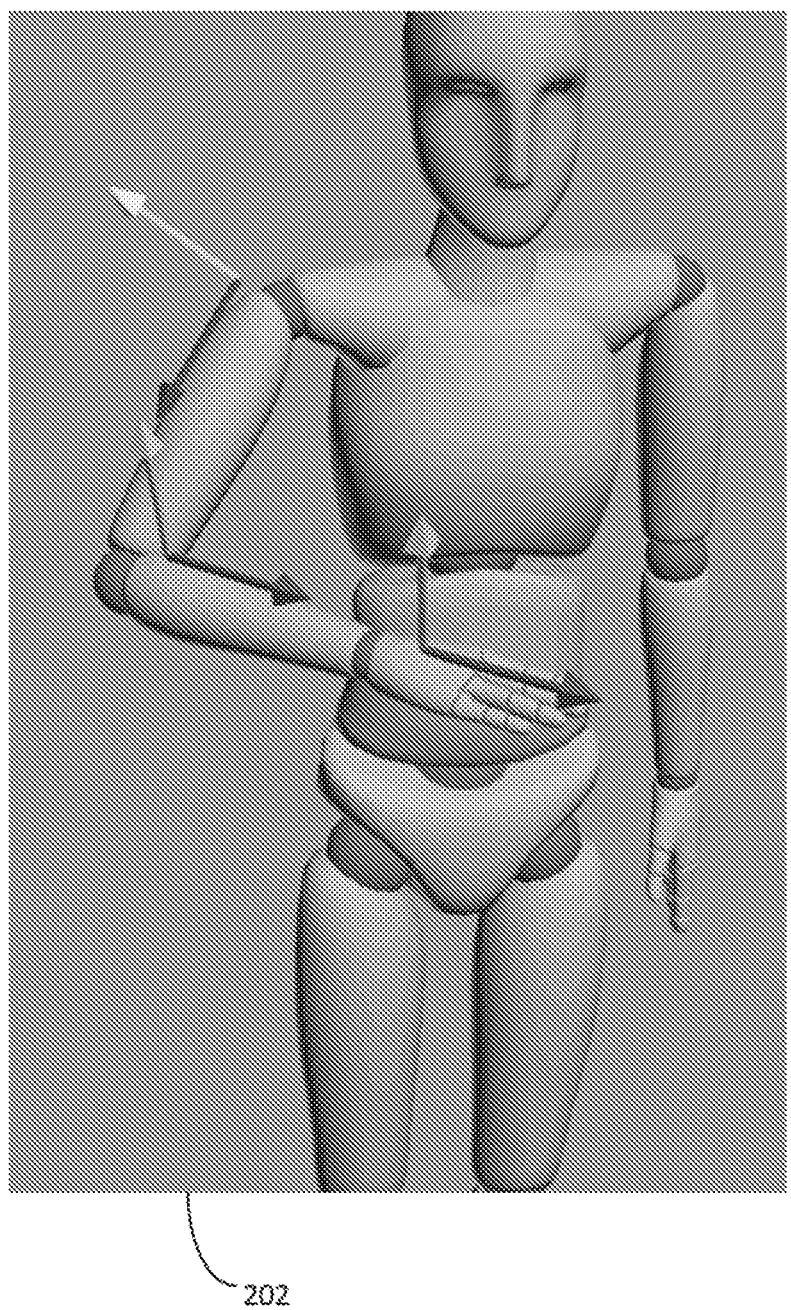
FIGS. 2 A-B illustrate an example of the Up and Forward measures changing as the wrist position changes, according to some embodiments.

The Figures described above are a representative set and are not an exhaustive with respect to embodying the invention.

DESCRIPTION

Disclosed are a system, method, and article for real time hand movement classification. The following description is presented to enable a person of ordinary skill in the art to make and use the various embodiments. Descriptions of specific devices, techniques, and applications are provided only as examples. Various modifications to the examples described herein can be readily apparent to those of ordinary skill in the art, and the general principles defined herein may be applied to other examples and applications without departing from the spirit and scope of the various embodiments.

Reference throughout this specification to "one embodiment," "an embodiment," 'one example,' or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

Furthermore, the described features, structures, or characteristics of the invention may be combined in any suitable manner in one or more embodiments. In the following description, numerous specific details are provided, such as examples of programming, software modules, user selections, network transactions, database queries, database structures, hardware modules, hardware circuits, hardware chips, etc., to provide a thorough understanding of embodiments of the invention. One skilled in the relevant art can recognize, however, that the invention may be practiced without one or more of the specific details, or with other methods, components, materials, and so forth. In other instances, well-known structures, materials, or operations are not shown or described in detail to avoid obscuring aspects of the invention.

The schematic flow chart diagrams included herein are generally set forth as logical flow chart diagrams. As such, the depicted order and labeled steps are indicative of one embodiment of the presented method. Other steps and methods may be conceived that are equivalent in function, logic, or effect to one or more steps, or portions thereof, of the illustrated method. Additionally, the format and symbols employed are provided to explain the logical steps of the method and are understood not to limit the scope of the method. Although various arrow types and line types may be employed in the flow chart diagrams, and they are understood not to limit the scope of the corresponding method. Indeed, some arrows or other connectors may be used to indicate only the logical flow of the method. For instance, an arrow may indicate a waiting or monitoring period of unspecified duration between enumerated steps of the depicted method. Additionally, the order in which a particular method occurs may or may not strictly adhere to the order of the corresponding steps shown.

Definitions

Example definitions for some embodiments are now provided.

Animatics can be a series of still images edited together and/or displayed in sequence with rough dialogue (e.g. scratch vocals) and/or rough soundtrack added to the sequence of still images to test said sound and/or images.

Augmented reality (AR) can be a live direct or indirect view of a physical, real-world environment whose elements are augmented (and/or supplemented) by computer-generated sensory input such as: sound, video, graphics and/or GPS data.

Body-position sensor can be any sensor that provides information used to determine the position of a specified location on a body based on, inter olio: position sensor systems (e.g. miniature inertial sensors, accelerometers, etc.), biomechanical models and/or sensor-fusion algorithms.

Classification is the problem of identifying to which of a set of categories (e.g. sub-populations) a new observation belongs, on the basis of a training set of data containing observations (e.g. instances) whose category membership is known. Example classification methods can include, inter alia: Linear classifiers (e.g. Fisher's linear discriminant, Logistic regression, Naive Bayes classifier, Perceptron, etc.); Support vector machines (e.g. Least squares support vector machines, etc.); Quadratic classifiers; Kernel estimation (e.g. k-nearest neighbor, etc.); Boosting (meta-algorithm) Decision trees (e.g. Random forests, etc.); Neural networks; Learning vector quantization; etc.

Cloud computing can involve deploying groups of remote servers and/or software networks that allow centralized data storage and online access to computer services or resources. These groups of remote serves and/or software networks can be a collection of remote computing services.

Haptic technology (e.g. kinesthetic communication) can apply forces, vibrations and/or motions to the user. This mechanical stimulation can create the perception of virtual objects by a user. Haptic devices may incorporate tactile sensors that measure forces exerted by the user on the interface.

Mobile device can be a smart phone, tablet computer, wearable computer (e.g. a smart watch, a head-mounted display computing system, etc.). In one example, a mobile device can be a small computing device, typically small enough to be handheld having a display screen with touch input and/or a miniature keyboard.

Motion capture can include the process of recording the movement of people, animals, vehicles, etc.

Radial basis function kernel (RBF kernel) is a kernel function used in various kernelized learning algorithms.

Real-time rendering can include various interactive areas of computer graphics that create synthetic images fast enough with a computer such that a viewer can interact with a virtual environment. The most common place to find real-time rendering is in video games.

Support vector machine can include supervised learning models with associated learning algorithms that analyze data used for classification and regression analysis. Given a set of training examples, each marked as belonging to one or the other of two categories, an SVM training algorithm builds a model that assigns new examples to one category or the other.

Visual effects (VFX) are the processes by which imagery can be created and/or manipulated outside the context of a live action shot. Visual effects can include the integration of live-action footage and generated imagery to create environments depicted in film, VR, AR, other virtual environments, etc.

Virtual Reality (VR) can include an immersive multimedia and/or computer-simulated life, replicates an environment that simulates physical presence in places in a world simulation and lets the user interact in that world. Virtual reality can also include creating sensory experiences, which can include, inter cilia: sight, hearing, touch, and/or smell.

Exemplary Systems and Methods

FIG. 1 illustrates an example process 100 for real time movement classification using a motion capture suit, according to some embodiments. In step 102, a time window of data consisting of the sensors X, Y and Z positions (e.g. X,Y,Z data) and the joints angles can be recorded. In step 104, process 100 can transform the angles to their corresponding frequency domain using fast Fourier transformation to remove the time dependency. In step 106, after data transformation, process 100 can train a support vector machine using the X,Y,Z data and the frequency data as input. In 108, process 100 can use the support vector machine to predict the body positions and movements in real time with compelling results.

Figure 2B:
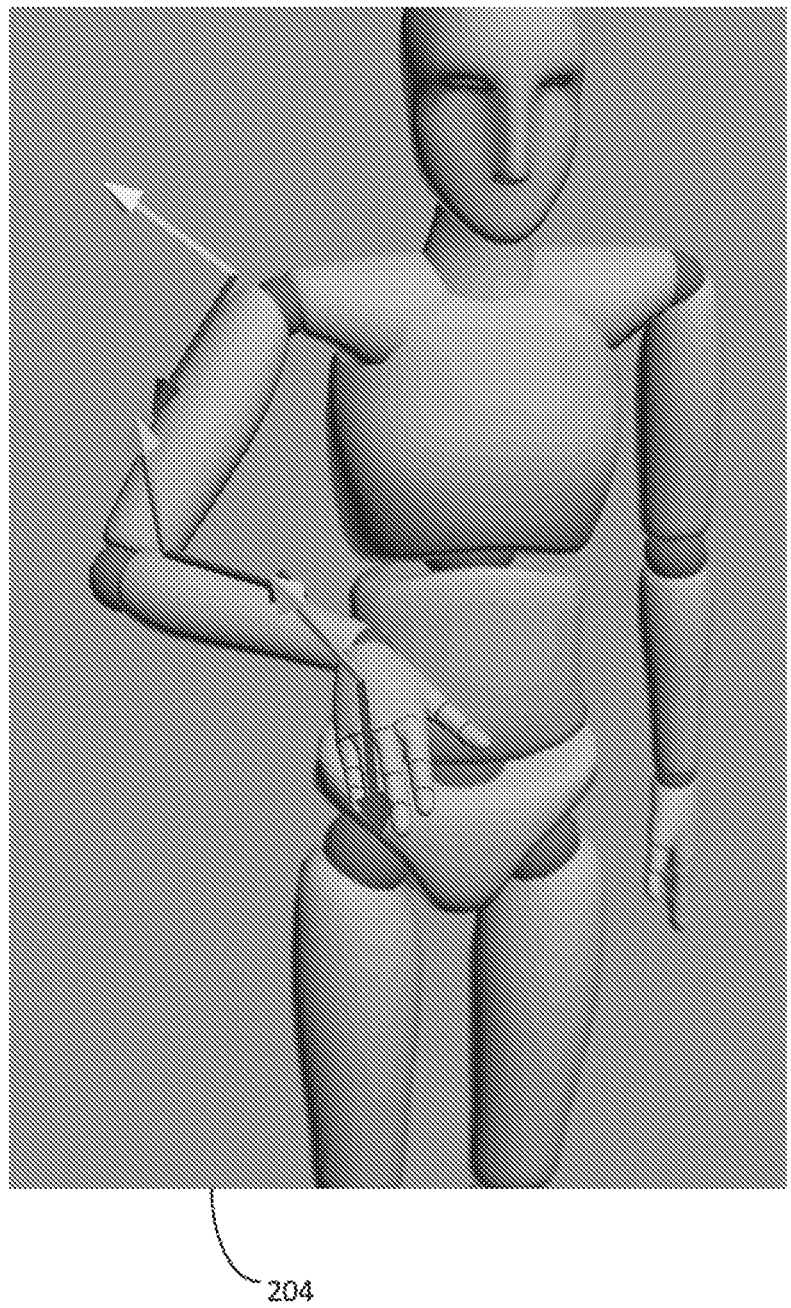

FIGS. 2 A-B illustrate an example of the Up and Forward measures changing as the wrist position changes, according to some embodiments. Data can be collected by having a person standing straight with the arms down the side with both palms facing the hip. This can be straight pose/start pose. The spine can be defined as the reference point for various (e.g. all) sensors. The sensors can initialize their starting position values according to the straight pose. The sensors relative X, Y and Z positions, their Up and Forward X, Y and Z positions, the angles between joints can then be obtained. For example, the angle at left lower leg can be thought of as the knee angle. Time can be measured by the hub when sampling is performed.

In one example, nineteen (19) sensors in total can be utilized, placed at: Hips, Left Upper Leg, Right Upper Leg, Left Lower Leg, Right Lower Leg, Left Foot, Right Foot, Spine, Chest, Neck, Head, Left Shoulder, Right Shoulder, Left Upper Arm, Right Upper Arm, Left Lower Arm, Right Lower Arm, Left Hand, Right Hand. The resulting data vector is on the form:

$$[(P_{x,y,z}, U_{x,y,z}, F_{x,y,z}), (\text{Angle}), (Hub-\text{time})]$$

with a total dimension of 19·3; 19·3; 19·3; 19·3; 1=191. It is noted that these example values can be modified in other example embodiments. The suit can potentially sample at around one-hundred (100) frames per second, but this amount of data may contain a lot of clustered data points, not carrying much new information. Accordingly, in one example, sixty (60) frames per second can be sampled, corresponding to the frame rate used in 1080p movies. This also means that process 200 can predict sixty (60) poses per second. It is worth noticing that due to the suit sending data via Wi-Fi, if the connection is unstable, 'hiccups' can be experience in the received data, an example of this is shown in FIG. 3.

FIG. 3 illustrates an example table 300, according to some embodiments. Table 300 can be an example of the hub time producing the same measurement per frame causing lag. As shown is the first position measurement and the last angle measurement of table 300. The remaining data points can be hidden.

Figure 4:
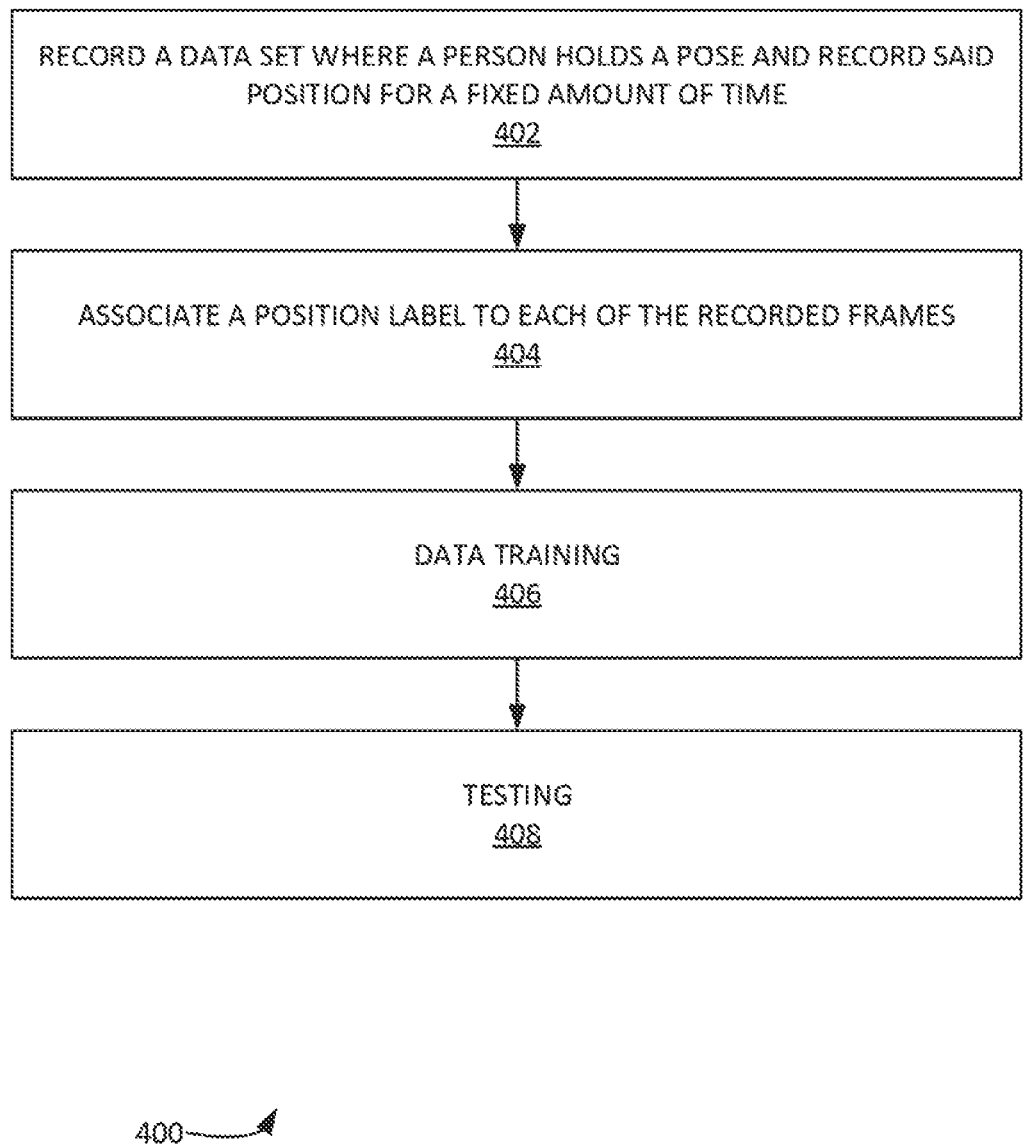
FIG. 4 illustrate an example process of a static positions classifier, according to some embodiments.

FIG. 4 illustrates an example process 400 of a static positions classifier; according to some embodiments. In some examples, a static positions classifier can exclude the angle and time data from the data set and focus on the position data. Process 400 can predict static positions. In step 402, process 400 can record a data set where a person holds a pose and record said position for a fixed amount of time. In step 404, process 400 can then associate a position label to each of the recorded frames. In step 406, training steps can be implemented on the data. In one particular example, data training can consist of obtaining information for fifteen (15) different poses with 74440 frames and 171 X, Y and Z positions resulting in 12.3 million data points. Process 400 can train two support vector machines with this data, one with a linear kernel, and one with an RBF kernel. Both models can be trained with a tolerance of ε=0:00001 and a one-vs-rest approach. The training time for the linear support vector machine can 20.34 seconds, and training time for the RBF support vector machine is 34.16 seconds. These are provided by way of example and not of limitation. It is noted that these example values can be modified in other example embodiments. In step 408, process 400 can implementing testing. For example, process 400 can now have 30054 frames of labeled test data. Testing on this can yield a linear accuracy of 99:9301% and an RBF accuracy of 99:9368%.

Figure 5:
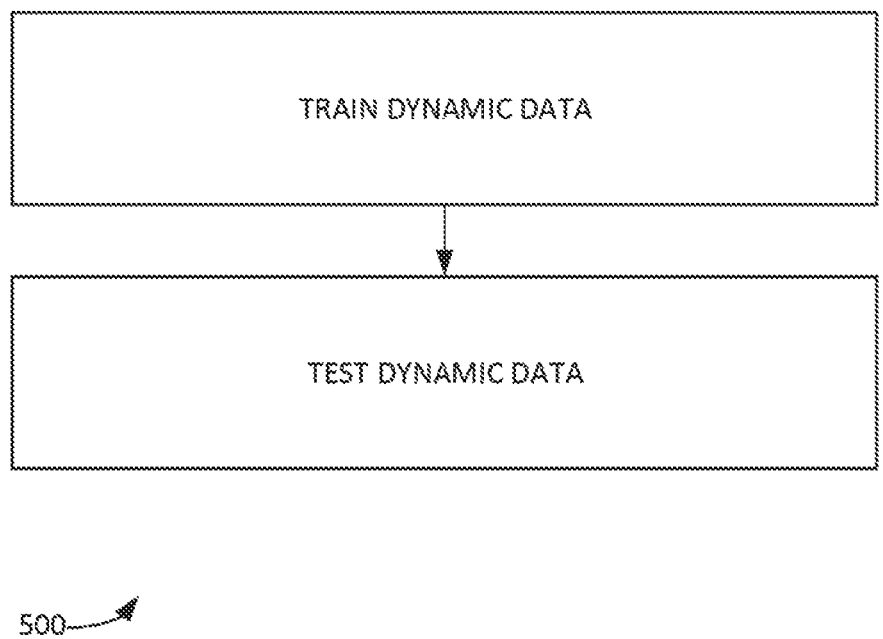
FIG. 5 illustrates an example process for a dynamic movement classifier, according to some embodiments.

FIG. 5 illustrates an example process 500 for a dynamic movement classifier, according to some embodiments. For the dynamic movements, process 500 can use a sliding window approach. Process 500 can plot the input data (e.g. with a window of size 80, corresponding to 1.33 seconds of data recorded, etc.).

A support vector machine can be trained on a square window may hold the dynamic position for too long. This problem is solved by using an exponential window of the form $e^{-\alpha \cdot frame}$ frame causing the oldest frames recorded to be dimmed by an exponential rate. This can cause the transitions between movements to be smoother. The time dimensions may be removed by using a Fourier transformation of the data. The Fast Fourier algorithm can use an orthonormal scale such that it can compare the amplitude across different movements. Finally, the absolute value of the output can be obtained, causing the imaginary signals to become real, and causing the negative amplitudes to be positive.

In one particular example, the three (3) largest frequencies per sensor can be kept. This can result in 3·19 frequencies per sliding window. In order to use the frequencies as input for the support vector machine, the frequencies matrix can be flattened and to obtain a fifty-seven (57) dimensional vector. This vector can be appended to the input vector to obtain a vector of length two-hundred and twenty-eight (228). It is noted that these example values can be modified in other example embodiments.

More specifically, in step 502, process 500 can train the dynamic data. In one example, the training data can consist of five (5) different poses, 21360 frames, with 171 X, Y and Z positions and 57 frequencies per frame, resulting in 228·21360=4.9 million data points. It is noted that these example values can be modified in other example embodiments. Two support vector machines can be trained with this data, one with a linear kernel, and one with an RBF kernel. Both models are trained with a tolerance of ε=0:00001 and a one-vs-rest approach. Training time for the linear support vector machine is 7.76 seconds and training time for the RBF support vector machine is 60.9 seconds.

In step 504, process 500 can have 10400 frames of labeled test data.

Merging of models (e.g. static and dynamic models, etc.) can be implemented. It is noted that the process supra may not have recorded any angular or hub-time data from the static positions, so it can be assumed that the corresponding frequencies are zero. This seems like a reasonable choice, a static position may not exercise any movement, thus having zero as the resulting frequencies. Accordingly, the static data can be artificially padded with zeroes yielding a static vector of dimension 228 and stacked the static data and the dynamic data on top of each other and train a support vector machine with this input.

This data can be trained. The training data can consist of fifteen (15) static poses and five (5) dynamic poses, with the same input as the dynamic classifier (e.g. 95800 frames in total). Two support vector machines can be trained, one with a linear kernel, and one with an RBF kernel. Both models are trained with a tolerance of ε=0:00001 and a one-vs-rest approach. Training time for the linear support vector machine can 69.44 seconds and training time for the RBF support vector machine is 452.43 seconds. These values are provided by way of example of not of limitation.

Training can then be implemented. The testing can consist of testing the combined classifier on first the static test data, and then the dynamic test data, (e.g. using 40454 labeled frames in total). In one example, the accuracy for the linear kernel can be 99.8%, and for the RBF kernel it is 84.52%. These values are provided by way of example of not of limitation.

The combined classifier has very good accuracy, both on the test data, but also testing in real time with a person that has not been used to record data.

The systems and methods herein provide framework for classifying movements. Adding a new movement to the model is a matter of recording it, labeling it, and retraining the support vector machine with it.

Hyper parameters are now discussed. For real time testing, one example can use α=−0:6. The dynamic movements can be predicted by a quick movement, so all fifty-seven (57) frequencies can be dampened by β=15%. There is a correlation between α and β, and the choice of these values can be further fine-tuned. Likewise, it might not be an exponential window that is the most efficient, but may be a different type of window (e.g. a linear window).

Simplification of data is now discussed. Data points may be extant that are not carrying any information, for instance the X, Y and Z positions of the spine is included, but may, by definition, be zero. Likewise, this may be the case with the chest and neck angle. Principal component analysis and/or other data analyzing techniques can be implemented on the sensor data, to exclude data points carrying neglectable information, thus simplifying the model.

Scalability is now discussed. As seen in the training results, the support vector machines run time increases exponential when more movements are added. A solution to this problem could be to rebuild the model to use a neural network.

Train and test data with movement transactions can be implemented. For example, the data can be recorded by a person doing a specific movement and nothing else. For example, in a real-time demonstration prediction problem can arise when there is a transact from one movement to another. Accordingly, train and test data can encapsulate this, and can yield a lower but more realistic accuracy.

Kernel tweaking is now discussed. Various results for the RBF can be refined by modifying the γ and C parameters. In one example, a polynomial or a sigmoid kernel can be utilized.

Additional Computing Systems

Figure 6:
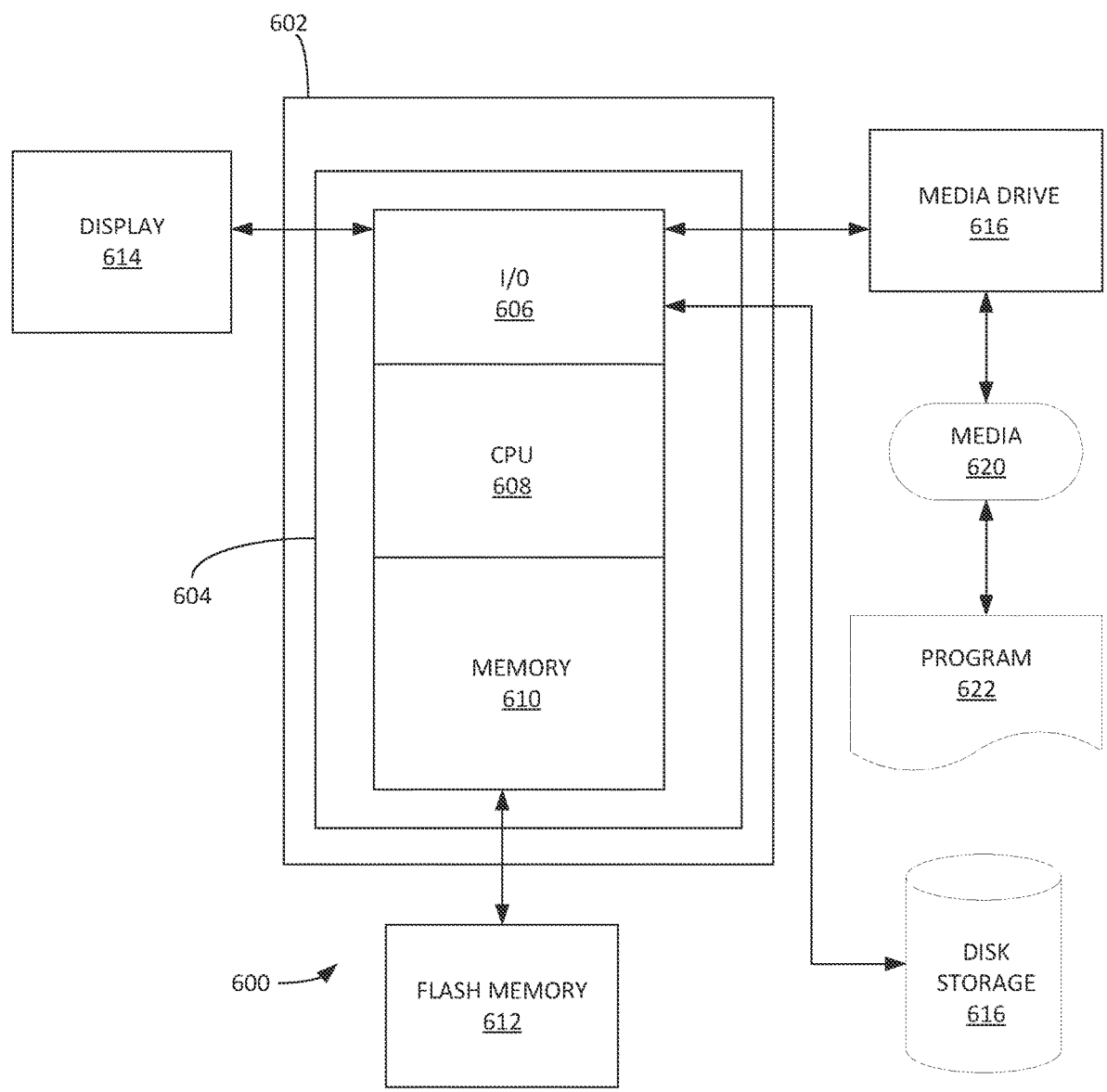
FIG. 6 depicts an exemplary computing system that can be configured to perform any one of the processes provided herein.

FIG. 6 depicts an exemplary computing system 600 that can be configured to perform any one of the processes provided herein. In this context, computing system 600 may include, for example, a processor, memory, storage, and I/O devices (e.g., monitor, keyboard, disk drive, Internet connection, etc.). However, computing system 600 may include circuitry or other specialized hardware for carrying out some or all aspects of the processes. In some operational settings, computing system 600 may be configured as a system that includes one or more units, each of which is configured to carry out some aspects of the processes either in software, hardware, or some combination thereof.

FIG. 6 depicts computing system 600 with a number of components that may be used to perform any of the processes described herein. The main system 602 includes a motherboard having an I/O section, one or more central processing units (CPU) 608, and a memory section 610, which may have a flash memory card 612 related to it. The I/O section 606 can be connected to a display 614, a keyboard and/or other user input (not shown), a disk storage unit 616, and a media drive unit 618. The media drive unit 618 can read/write a computer-readable medium 620, which can contain programs 622 and/or data. Computing system 600 can include a web browser. Moreover, it is noted that computing system 600 can be configured to include additional systems in order to fulfill various functionalities. Computing system 600 can communicate with other computing devices based on various computer communication protocols such a Wi-Fi, Bluetooth® (and/or other standards for exchanging data over short distances includes those using short-wavelength radio transmissions), USB, Ethernet, cellular, an ultrasonic local area communication protocol, etc.

Figure 7:
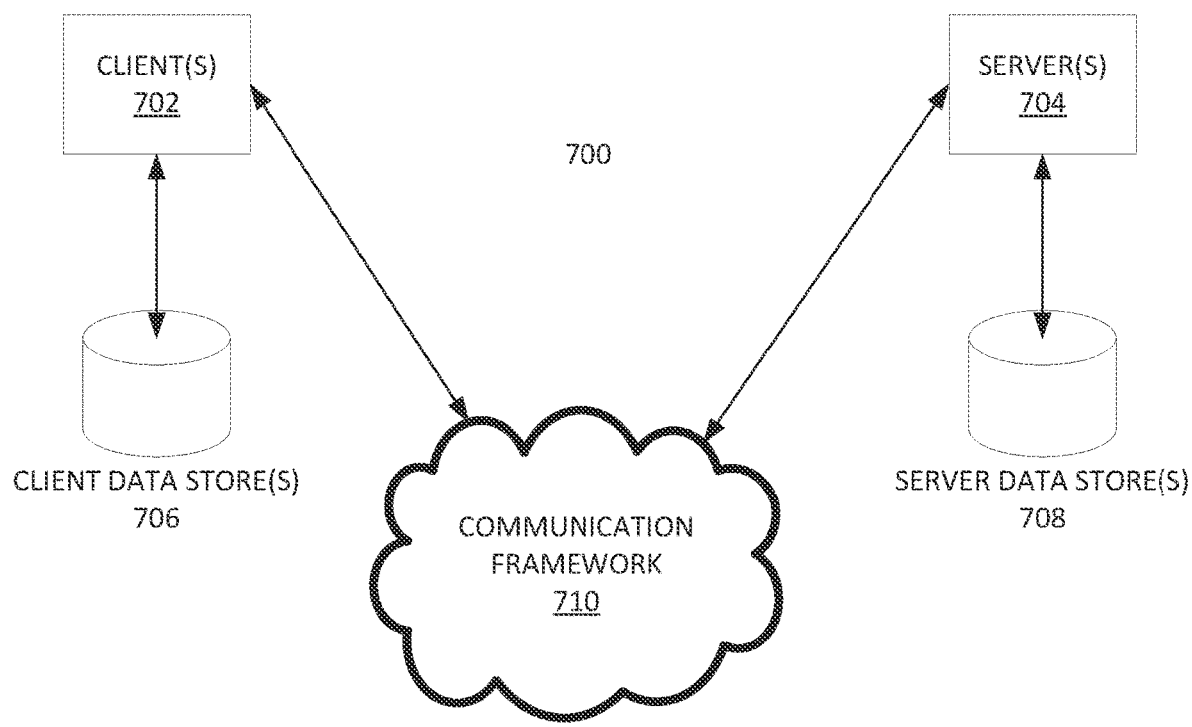
FIG. 7 is a block diagram of a sample-computing environment that can be utilized to implement various embodiments.

FIG. 7 is a block diagram of a sample computing environment 700 that can be utilized to implement various embodiments. The system 700 further illustrates a system that includes one or more client(s) 702. The client(s) 702 can be hardware and/or software (e.g., threads, processes, computing devices). The system 700 also includes one or more servers) 704. The server(s) 704 can also be hardware and/or software (e.g., threads, processes, computing devices). One possible communication between a client 702 and a server 704 may be in the form of a data packet adapted to be transmitted between two or more computer processes. The system 700 includes a communication framework that can be employed to facilitate communications between the client(s) 702 and the server(s) 704. The client(s) 702 are connected to one or more client data store(s) 706 that can be employed to store information local to the client(s) 702. Similarly, the server(s) 704 are connected to one or more server data store(s) 708 that can be employed to store information local to the server(s) 704. In some embodiments, system 700 can instead be a collection of remote computing services constituting a cloud-computing platform.

Hand Gesture Recognition Process

Figure 8:
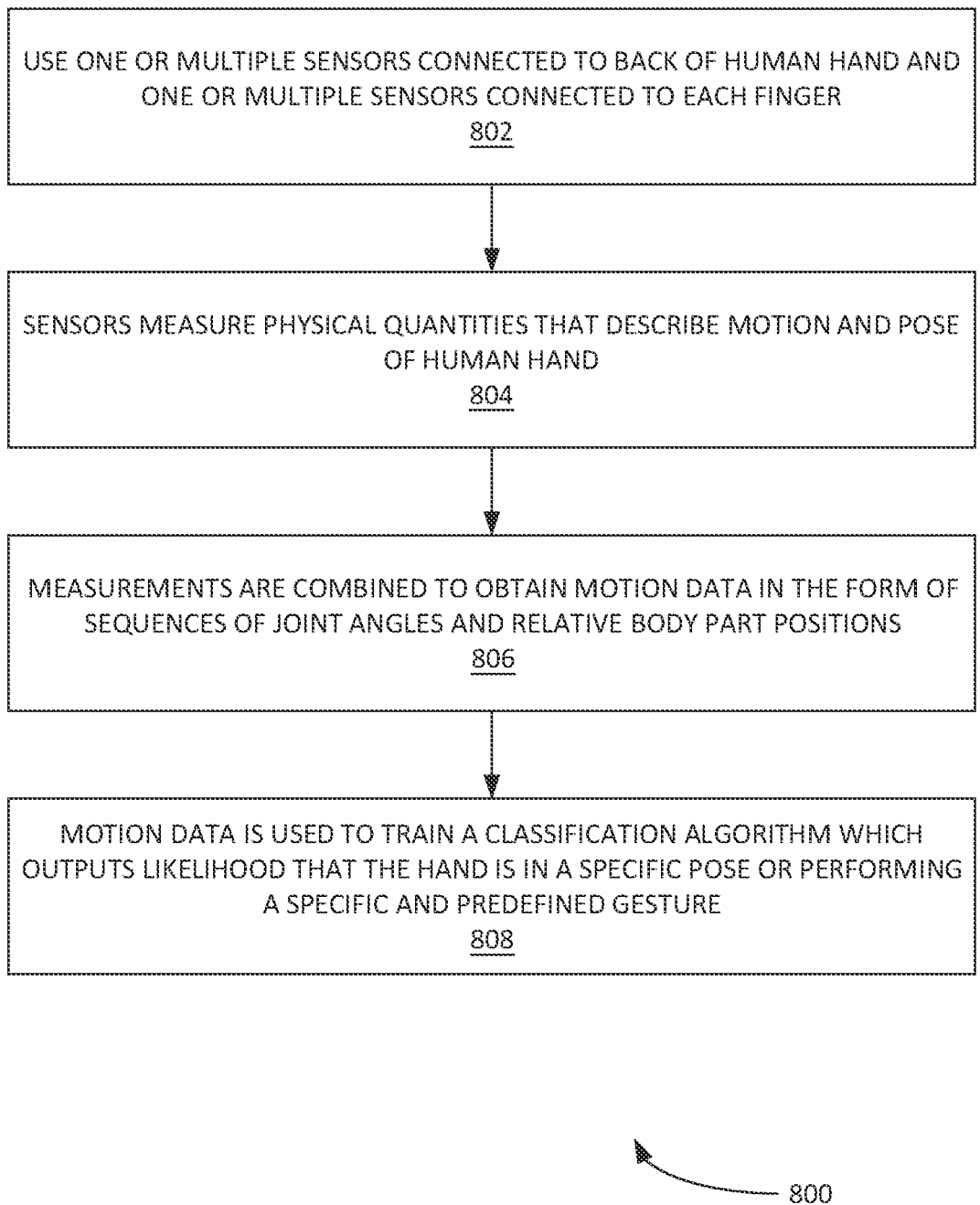
FIG. 8 illustrates an example process for hand gesture recognition, according to some embodiments.

FIG. 8 illustrates an example process 800 for hand gesture recognition, according to some embodiments. In some examples, process 800 can adapt the methods and systems provided supra for a motion capture glove. Process 800 can utilize a hand gesture recognition system, which is an extension of a body gesture recognition system algorithm. This extension applies various gesture recognition techniques. In step 802 can, process 800 can use one or multiple sensors connected to the back of the human hand and one or multiple sensors connected to each finger. In step 804, the sensors measure physical quantities that describe the motion and pose of the human hand. These can be, inter alia: a user's relative position to each other through internally generated magnetic field strengths, the user's relative acceleration in global space, the user's rotational velocity or other physical quantities, etc. In step 806, these measurements can then be combined to obtain motion data in the form of sequences of joint angles and relative body part positions. In step 808, this motion data is then used to train a classification algorithm which outputs the likelihood that the hand is in a specific pose or performing a specific and predefined gesture.

Conclusion

Although the present embodiments have been described with reference to specific example embodiments, various modifications and changes can be made to these embodiments without departing from the broader spirit and scope of the various embodiments. For example, the various devices, modules, etc. described herein can be enabled and operated using hardware circuitry, firmware, software or any combination of hardware, firmware, and software (e.g., embodied in a machine-readable medium).

In addition, it can be appreciated that the various operations, processes, and methods disclosed herein can be embodied in a machine-readable medium and/or a machine accessible medium compatible with a data processing system (e.g., a computer system), and can be performed in any order (e.g., including using means for achieving the various operations). Accordingly, the specification and drawings are to be regarded in an illustrative rather than a restrictive sense. In some embodiments, the machine-readable medium can be a non-transitory form of machine-readable medium.

What is claimed is:

1. A computerized process useful or movement classification using a motion capture suit, comprising:
providing the motion capture suit worn by a user, wherein the motion capture suit comprises a set of position sensors and a Wi-Fi system configured to communicate a set of position sensor data to a computing system;
providing the computing system to:
receive a set of position data from the motion capture suit for a specified time window of data comprising X, Y and Z axis positions and a joints-angle data for each position sensor of the set of position sensors, transforming each joints-angle data to a corresponding frequency domain using a fast Fourier transformation to remove any time dependency value, after the fast Fourier data transformation, train a support vector machine using the X, y and Z axis positions data arid the frequency domain data as input, using the support vector machine to predict a set of body positions and movements.

2. The computerized process of claim 1, wherein the set of position sensors are placed at: each hip of the user wearing the motion capture suit, an left upper leg, a right upper leg, a left lower leg, a right lower leg, a left foot, a right foot, a spine region, a chest region, a neck, a head, a left shoulder, a right shoulder, a left upper arm, a right upper arm, a left lower arm, a right lower arm, a left hand, and a right hand.

3. The computerized process of claim 2, wherein the set of position data is received from the motion capture suit at a sample to sixty (60) frames per second.

4. The computerized process of claim 3, wherein the support vector machine to predict a set of body positions and movements in real time.

5. The computerized process of claim 4, wherein two support vector machines are trained.

6. The computerized process of claim 5, wherein the two support vector machines comprise a first support vector machine with a linear kernel, and a second support vector machine with an RBF kernel.

7. The computerized process of claim 6 further comprising:
using a static positions classifier that predicts one or more static positions using the position data and excluding the joints-angle data and time data from the data set.

8. The computerized process of claim 7 further comprising:
using a dynamic movement classifier that use a sliding window approach to predict dynamic movements.

9. The computerized process of claim 8 further comprising:
merging the output of the static positions classifier and the output of the dynamic movement classifier into a combine data set that is used to train the support vector machine.

10. The computerized process of claim 9, wherein the training data comprises fifteen (15) static poses and five (5) dynamic poses.

11. A computerized system useful for real time movement classification using a motion capture suit, comprising:
at least one processor configured to execute instructions;
memory containing instructions that when executed on the processor, causes the at least one processor to perform operations that:
providing the motion capture suit worn by a user, wherein the motion capture suit comprises a set of position sensors and a Wi-Fi system configured to communicate a set of position sensor data to a computing system;
providing the computing system to:
receive a set of position data from the motion capture suit for a specified time window of data comprising X, Y and Z axis positions and a joints angle for each position sensor of the set of position sensors,
transforming each joint angle to a corresponding frequency domain using a fast Fourier transformation to remove any time dependency value,
after the fast Fourier data transformation, train a support vector machine using the X, Y and Z axis positions data and the frequency domain data as input,
using the support vector machine to predict a set of body positions and movements.

12. The computerized system of claim 11, wherein the set of position sensors are placed at: each hip of the user wearing the motion capture suit, an left upper leg, a right upper leg, a left lower leg, a right lower leg, a left foot, a right foot, a spine region, a chest region, a neck, a head, a left shoulder, a right shoulder, a left upper arm, a right upper arm, a left lower arm, a right lower arm, a left hand, and a right hand.

13. The computerized system of claim 12, wherein the set of position data is received the motion capture suit at a sample to sixty (60) frames per second.

14. The computerized system of claim 13, wherein the support vector machine to predict a set of body positions and movements in real time.

15. The computerized system of claim 14, wherein two support vector machines are trained.

16. The computerized system of claim 15, wherein the two support vector machines comprise a first support vector machine with a linear kernel, and a second support vector machine with an RBF kernel.

17. The computerized system of claim 16, wherein memory containing instructions when executed on the processor, causes the at least one processor to perform operations that:
use a static positions classifier that predicts one or more static positions using the position data and excluding the joints-angle data and time data from the data set.

18. The computerized system of claim 17, wherein memory containing instructions that when executed on the processor, causes the at least one processor to perform operations that:
use a dynamic movement classifier hat use a sliding window approach to predict dynamic movements.

19. The computerized system of claim 18, wherein memory containing instructions that when executed on the processor, causes the at least one processor to perform operations that:
merge the output of the static positions classifier and the output of the dynamic movement classifier into a combine data set that is used to train the support vector machine.

20. The computerized system of claim 19, wherein the training data comprises fifteen (15) static poses and five (5) dynamic poses.

* * * * *